(12) United States Patent
Ross et al.

(10) Patent No.: US 6,688,745 B2
(45) Date of Patent: Feb. 10, 2004

(54) SUBJECTIVE REFINEMENT OF WAVEFRONT MEASUREMENTS

(75) Inventors: Denwood F. Ross, Austinburg, OH (US); Josef Bille, Heidelberg (DE); Michael Schottner, Leimen (DE); Frank Mueller, Speyer (DE)

(73) Assignee: Johnson & Johnson Vision Care, Inc., Jacksonville, FL (US)

(*) Notice: Subject to any disclaimer, the term of this patent is extended or adjusted under 35 U.S.C. 154(b) by 46 days.

(21) Appl. No.: 10/032,836

(22) Filed: Oct. 25, 2001

(65) Prior Publication Data

US 2003/0081174 A1 May 1, 2003

(51) Int. Cl.[7] .................................................. A61B 3/14
(52) U.S. Cl. ....................................... 351/206; 351/212
(58) Field of Search ................................. 351/205, 206, 351/211, 212, 221, 246; 606/4, 5; 356/124

(56) References Cited

U.S. PATENT DOCUMENTS

| | | | |
|---|---|---|---|
| 4,105,302 A | 8/1978 | Tate, Jr. | |
| 4,838,679 A | 6/1989 | Bille | 351/205 |
| 5,062,702 A | 11/1991 | Bille | 351/212 |
| 5,177,511 A | 1/1993 | Feuerstein et al. | 351/205 |
| 5,777,719 A | 7/1998 | Williams et al. | 351/212 |
| 5,785,704 A | 7/1998 | Bille et al. | 606/17 |
| 5,949,521 A | 9/1999 | Williams et al. | 351/246 |
| 6,095,651 A | 8/2000 | Williams et al. | 351/246 |
| 6,155,684 A | 12/2000 | Bille et al. | |
| 6,271,915 B1 * | 8/2001 | Frey et al. | 356/124 |
| 6,394,605 B1 * | 5/2002 | Campin et al. | 351/246 |

FOREIGN PATENT DOCUMENTS

| | | | |
|---|---|---|---|
| DE | 42 22 395 A1 | 1/1994 | A61B/3/103 |
| WO | WO 99/27334 | 6/1999 | |

OTHER PUBLICATIONS

G. Walsh, W.N. Charman and H.C. Howland, "Objective technique for the determination of monochromatic aberrations of the human eye", Sep. 1984, vol. 1, No. 9, pp. 987–992.

Andreas W. Dreher, Josef F. Bille, and Robert N. Weinreb, "Active optical depth resolution improvement of the laser tomographic scanner", Feb. 15, 1989, vol. 28, No. 4, pp. 804–808.

W.N. Charman, "Wavefront Aberration of the Eye: A Review", Optometry and Vision Science, Symposium Paper, Feb. 26, 1991, vol. 68, No. 8, pp. 574–583.

Junzhong Liang, Bernhard Grimm, Stefan Goelz, and Josef F. Bille, "Objective measurement of wave aberrations of the human eye with the use of Hartman–Shack wave–front sensor", Jul. 1994, vol. 37, No. 3, 1 page.

D.R. Williams and J. Liang, "Adaptive Optics For High Resolution Retinal Imaging", Feb. 15, 1996, vol. 37, No. 3, 1 page.

Josef F. Bille, Andreas W. Dreher; and Gerhard Zinser, "Scanner Laser Tomography of the Living Human Eye", Chapter 28, pp. 528–547, date unknown.

(List continued on next page.)

*Primary Examiner*—George Manuel

(57) ABSTRACT

Apparatus and method for subjectively refining a corrective prescription based on feedback from a patient. Subjective refinement of a corrective prescription is accomplished by measuring aberrations of a wavefront emanating from the eye, computing a proposed corrective prescription based on the measured aberrations presenting to the patient an image reflecting the proposed corrective prescription, and varying the proposed corrective prescription based on feedback from the patient through an input device coupled to the processor to obtain the preferred corrective prescription.

6 Claims, 4 Drawing Sheets

OTHER PUBLICATIONS

Dirk–Uwe Bartsch, Ph.D., Gerhard Zinser, Ph.D., and William R. Freeman, M.D., "Resolution Improvement in Confocal Scanning Laser Tomography of the Human Fundus", pp. 134–137, date unknown.

PCT International Search Report dated Jul. 17, 2003, for PCT Appln. No. PCT/US 02/33205.

Bille J F: "Preoperative simulation of outcomes using adaptive optics" Journal of Refractive Surgery, Thorofare, NJ. US, vol. 16, No. 5, Sep. 2000(2000–9), pp. S608–S610. XP002240671 ISSN: 1081–597X p. S608, left–hand column, line 11–right–hand column, line 11.

Haddrill Marilyn: "Wavefront sensors may soon be used as sophisticated autofractors but provide much more" EYEWORLD, 'Online! Oct. 10, 2001(Oct. 10, 2001), XP002246579 Retrieved from the Internet: <URL:http://www.eyeworld.org.oct01/1001p67.html>'retrieved on Jul. 4, 2003, p. 2, line 113–p. 3, line 17.

Wilkes S C et al: "High resolution adaptive optics test bed for vision science" ADAPTIVE OPTICS SYSTEMS AND TECHNOLOGY II, San Diego, CA, USA, Jul. 30–Aug. 1, 2001, vol. 4494, pp. 349–356, XP008019280 Proceedings of the SPIE—The International Society of Optical Engineering, 2002, SPIE–Int. Soc. Opt. Eng. USA ISSN: 0277–786X p. 353.

* cited by examiner

FIG. 1 _PRIOR ART_

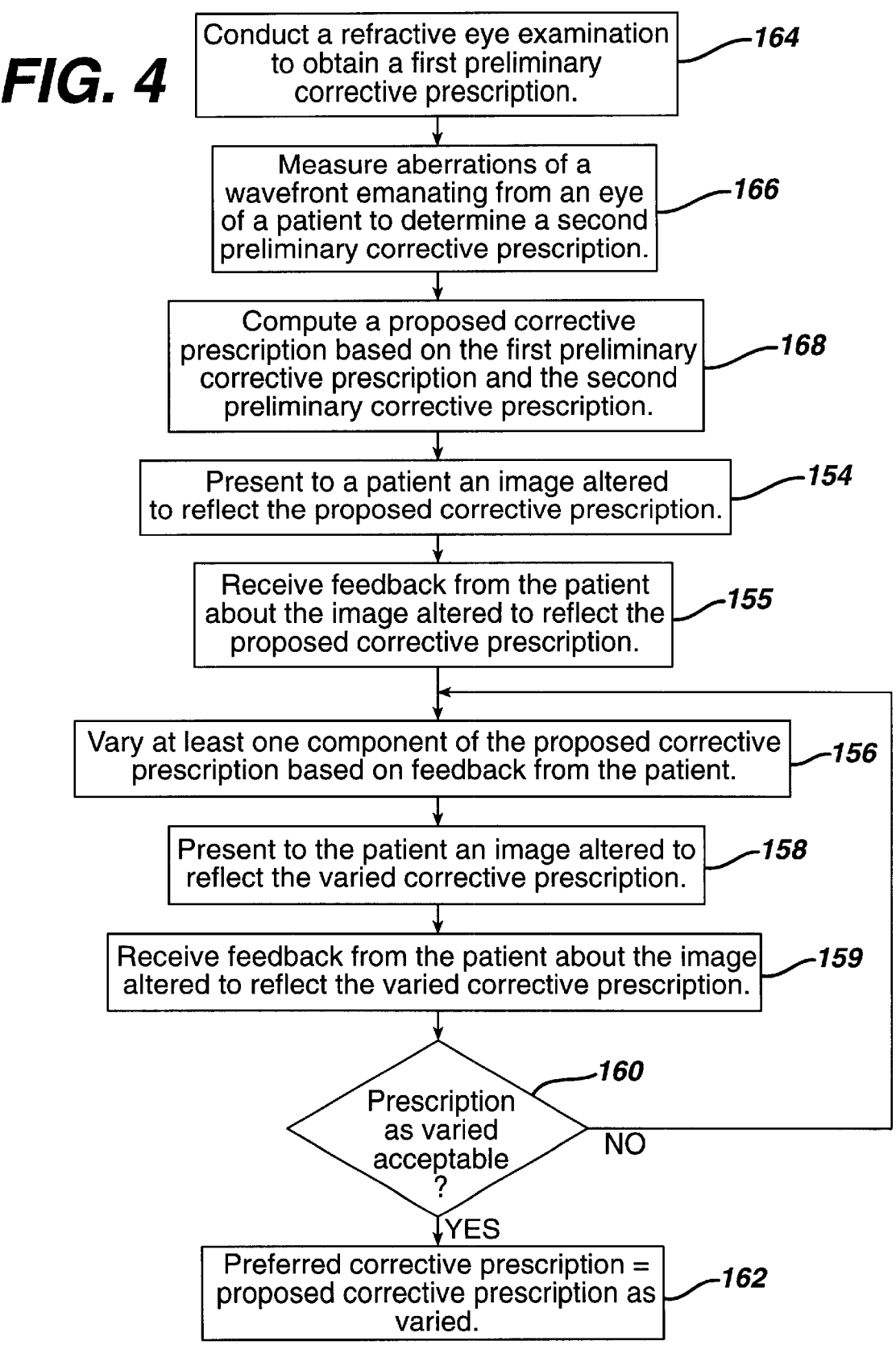

SUBJECTIVE REFINEMENT OF WAVEFRONT MEASUREMENTS

FIELD OF THE INVENTION

The present invention relates to optical instruments for developing a corrective ophthalmic prescription and, more particularly, to apparatuses and methods for subjectively refining a corrective prescription based on aberrations determined by a wavefront measuring device (WMD).

BACKGROUND OF THE INVENTION

The eye is an optical system having several optical elements for focusing light rays representing images onto the retina within the eye. The sharpness of the images produced on the retina is a factor in determining the visual acuity of the eye. Imperfections within the lens and other components and material within the eye, however, may cause the light rays to deviate from the desired path. These deviations, referred to as aberrations, result in blurred images and decreased visual acuity. Hence, methods and apparatuses for measuring aberrations are used to aid in the correction of such problems.

One method of detecting aberrations introduced by the eye involves the determination of aberrations introduced into light rays exiting from the eye. An input beam of light focused into the eye to a point on the retina is reflected or scattered back out of the eye as a wavefront. The wavefront contains the aberrations introduced as the wavefront passes through the eye's optical elements and exits the eye. By determining the propagation direction of discrete portions (i.e., samples) of this wavefront, the aberrations can be determined, thereby enabling the production of corrective lenses and/or performance of other corrective procedures that restore visual acuity.

FIG. 1 is an illustration of a prior art WMD 10 for measuring aberrations within a wavefront 100 and correcting aberrations. An input beam 102 generated by a radiation source 104 (e.g., a laser) is routed to an eye 106 by a beam splitter 108 where it is focused to a small spot 110 on the retina 112 within the eye 106. The wavefront 100 reflected from the spot 110 on the retina 112, which acts as a diffuse reflector, becomes aberrated as it passes through the lens and other components and materials within the eye 106. In an ideal eye, the wavefront 100 would be free of aberrations. In an imperfect eye 106, however, aberrations are introduced as the wavefront 100 passes out of the eye 106 and results in an imperfect wavefront containing aberrations.

On the return path, the wavefront 100 passes through the beam splitter 108 to a sensor 114 that includes, for example, a Hartman-Shack lenslet array 116 and an imaging device 118 containing a charge coupled device (CCD). A quarter-wave plate 120, positioned between the eye 106 and the beam splitter 108, is a known technique for manipulating the polarization of the input beam 102 going into the eye 106 and the wavefront 100 emanating from the eye 106 to allow the wavefront 100 to pass through the beam splitter 108 toward the wavefront sensor 114. Additional lenses 122 are positioned between the eye 106 and the wavefront sensor 114 to image the plane of the pupil of the eye 106 onto the wavefront sensor 114 with a desired magnification. Information detected by the wavefront sensor 114 is then processed by a processor 124 to determine the aberrations of the wavefront 100, which can be used to develop a corrective prescription for the eye 106.

While the WMD 10 depicted in FIG. 1 is able to determine aberrations introduced by the eye 106 with a high degree of accuracy, the development of a corrective prescription needs to be precisely tailored to a patient's visual needs. In addition, vision correction involves a perceptual aspect (i.e., psychophysics) that cannot be captured with conventional WMDs. It is therefore desirable to obtain subjective feedback from the patient during the development of the corrective prescription. Accordingly, methods and apparatuses for subjectively refining corrective prescriptions based on aberrations determined by WMDs are needed. The present invention fulfills this need among others.

SUMMARY OF THE INVENTION

The present invention discloses methods and apparatuses for subjectively refining corrective prescriptions based on aberrations determined by WMDs. In the present invention, an image is altered to reflect the corrective prescription and presented to a patient. Feedback is received from the patient to vary the corrective prescription, and further alter the image, which is again presented to the patient for further feedback. This process is repeated until the image presented to the patient is acceptable to the patient. The corrective prescription at this point becomes the patient's preferred corrective prescription.

One aspect of the present invention is a method for obtaining a preferred corrective prescription for an eye of a patient. The method includes measuring aberrations of a wavefront emanating from the eye, computing a proposed corrective prescription based on the measured aberrations, presenting to the patient an image altered to reflect the proposed corrective prescription, receiving feedback from the patient about the image altered to reflect the proposed corrective prescription, varying the proposed corrective prescription based on feedback from the patient, presenting to the patient an image altered to reflect the varied corrective prescription, and receiving feedback from the patient about the image altered to reflect the varied corrective prescription. The corrective prescription is then varied based on feedback from the patient and an image altered to reflect the varied corrective prescription is presented to the patient for feedback, repeatedly, to obtain the preferred corrective prescription.

Another aspect of the present invention is an apparatus for obtaining a preferred corrective prescription for an eye of a patient. The apparatus includes a WMD capable of measuring aberrations of the eye, a processor configured to determine a proposed corrective prescription including one or more components based on the measured aberrations, a display device to present an image reflecting the corrective prescription to the patient, and an input device capable of varying at least one of the one or more components based on feedback from the patient to obtain the preferred corrective prescription.

BRIEF DESCRIPTION OF THE DRAWINGS

FIG. 4 is a flow chart of an alternative wavefront measuring method for subjectively refining a corrective prescription in accordance with the present invention.

DETAILED DESCRIPTION OF THE INVENTION

Figure 2:
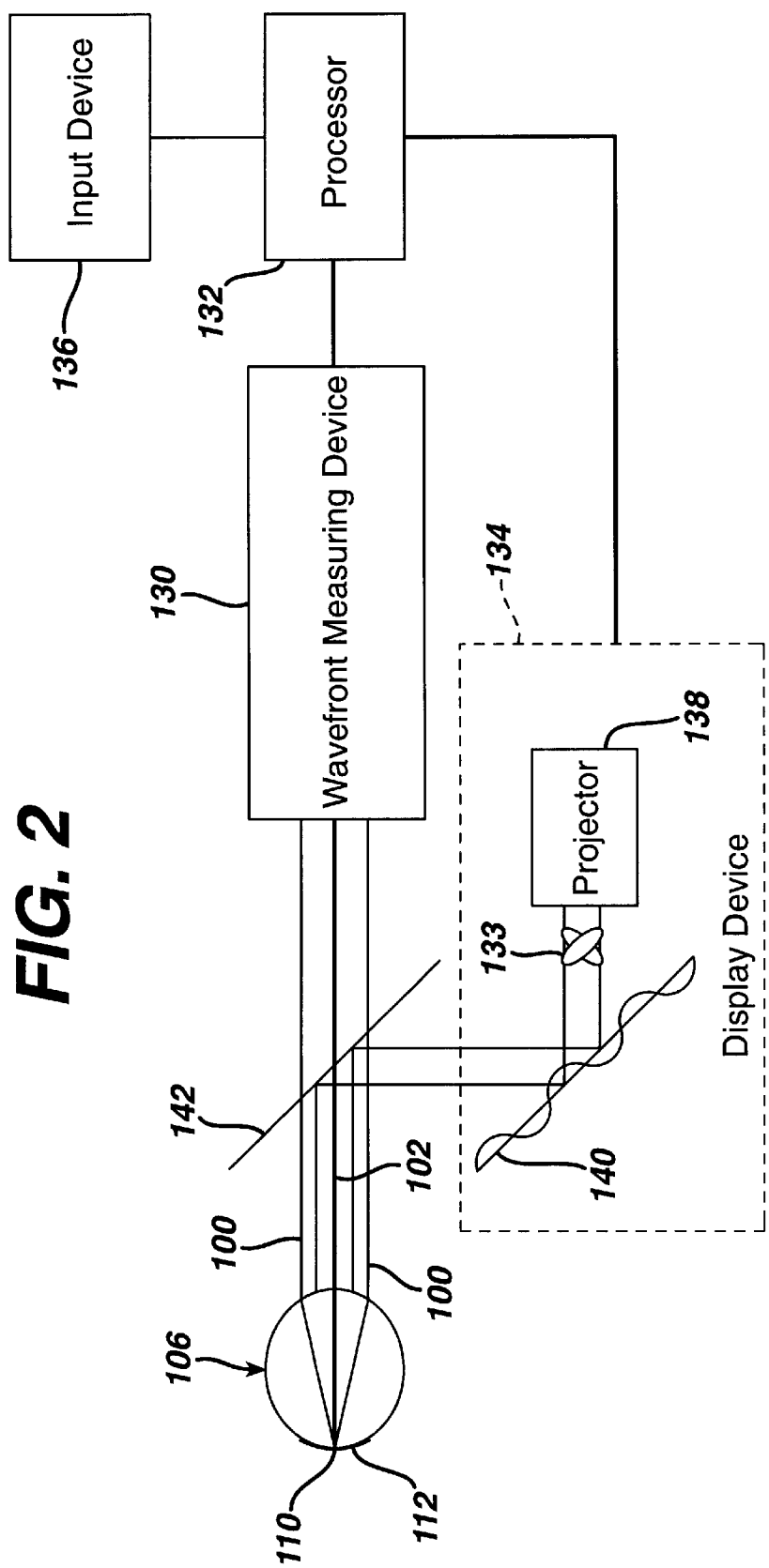
FIG. 2 is a block diagram of a wavefront measuring system capable of subjectively refining a corrective prescription in accordance with the present invention.

Illustrated in FIG. 2 is an ophthalmic wavefront measuring system capable of receiving feedback from a patient to subjectively refine a corrective prescription based on aberrations measured by a WMD 130. In a general overview of this embodiment, the WMD 130 generates an input beam 102 that is directed into the eye 106 and reflected to produce a wavefront 100 that travels back out of the eye 106. Aberrations within the wavefront 100 are measured by the WMD 130. A processor 132 receives the aberration information from the WMD 130 and develops a proposed corrective prescription. An image 133 altered in accordance with the proposed corrective prescription is then presented to the patient via a display device 134. The patient views the image 133 and provides feedback related to the proposed corrective prescription through an input device 136 to vary components of the proposed corrective prescription. An image 133 is then altered in accordance with the varied corrective prescription and presented to the patient for further feedback until a final preferred corrective prescription is achieved. The wavefront measuring system of the present embodiment is now described in more detail below.

The WMD 130 captures information related to aberrations of the eye 106. In the illustrated embodiment, the WMD 130 is coupled to the corrective processor 132 to pass the captured information directly to it. Alternatively, the captured information can be stored on a computer readable medium such as a floppy disk by the WMD 130 for transfer to the corrective processor 132. The WMD 130 may be a WMD of a conventional type such as the Complete Ophthalmic Analysis System™ produced by Wavefront Sciences, Inc.

The corrective processor 132 analyzes the captured aberration information from the WMD 130 to produce a proposed corrective prescription for the eye 106. It also analyzes feedback received through the input device 136 to vary the proposed corrective prescription. The corrective processor develops a signal for displaying an image 133 at the display device 134 that reflects the corrective prescription as proposed and varied. The corrective prescriptions may include aberration components such as a sphere, cylinder, and axis of conventional aberrations (i.e., defocus and astigmatism). In addition, the corrective prescriptions may include aberration components of nonconventional aberrations such as spherical aberrations, coma, trefoil, tetrafoil, and pentafoil. The corrective prescriptions may be represented using Seidel and/or Zernike coefficients. Alternatively, the corrective prescriptions may be represented using an optical path difference (OPD) measurement.

The input device 136 receives the feedback from a patient. In the illustrated embodiment, the input device 136 is coupled to the corrective processor 132, and may be any conventional input device such as a joystick, keyboard, light pen, microphone, or essentially any device capable of transforming information from the patient into information suitable for processing by the processor 132.

The display device 134 is configured to receive the signal from the processor 132 and display an image 133 altered to reflect the prescription determined by the processor 132. The image 133 is altered to a particular prescription so that the image 133 appears to the eye 106 as if it were corrected without the use of corrective eye wear. In the illustrated embodiment, the display device 134 includes a projector 138 to project the image 133 and an adaptive optical device 140 to alter the image 133. In an alternative embodiment, the display device 134 is a monitor that displays an image simulating the effect of varying components of the proposed corrective prescription.

The image 133 is a target or object with sufficient detail to allow a patient to detect aberration changes. In one embodiment, the size of the image 133 is such that the eye 106 can fixate on the image 133 as altered, thereby allowing aberrations to be determined for on-axis central, steady fixation. In an alternative embodiment, a central fixation point is marked on the image 133 to prevent the eye from being drawn off-axis due to the size of the image 133. It is contemplated that a system that tracks movements of the eye 106 and compensates for off-axis aberration measurements could be employed, thereby allowing the use of images that may draw the eye off-axis.

The projector 138 may be a known projector and may include conventional lenses for collimating the projected image 133. The adaptive optical device 140 is a device capable of modifying the image 133 projected by the projector 138 based on the signal from the processor 132. By configuring the adaptive optical device 140, the projected image 133 displayed to the eye 106 can be altered. The adaptive optical device 140 can be a known deformable mirror having a surface that deforms in response to the signal from the corrective processor 132 to modify the projected image 133 deflected off it. In alternative embodiments, the adaptive optical device 140 may be a liquid crystal device, a micro machine mirror, or other suitable device capable of modifying the projected image 133.

Figure 1:
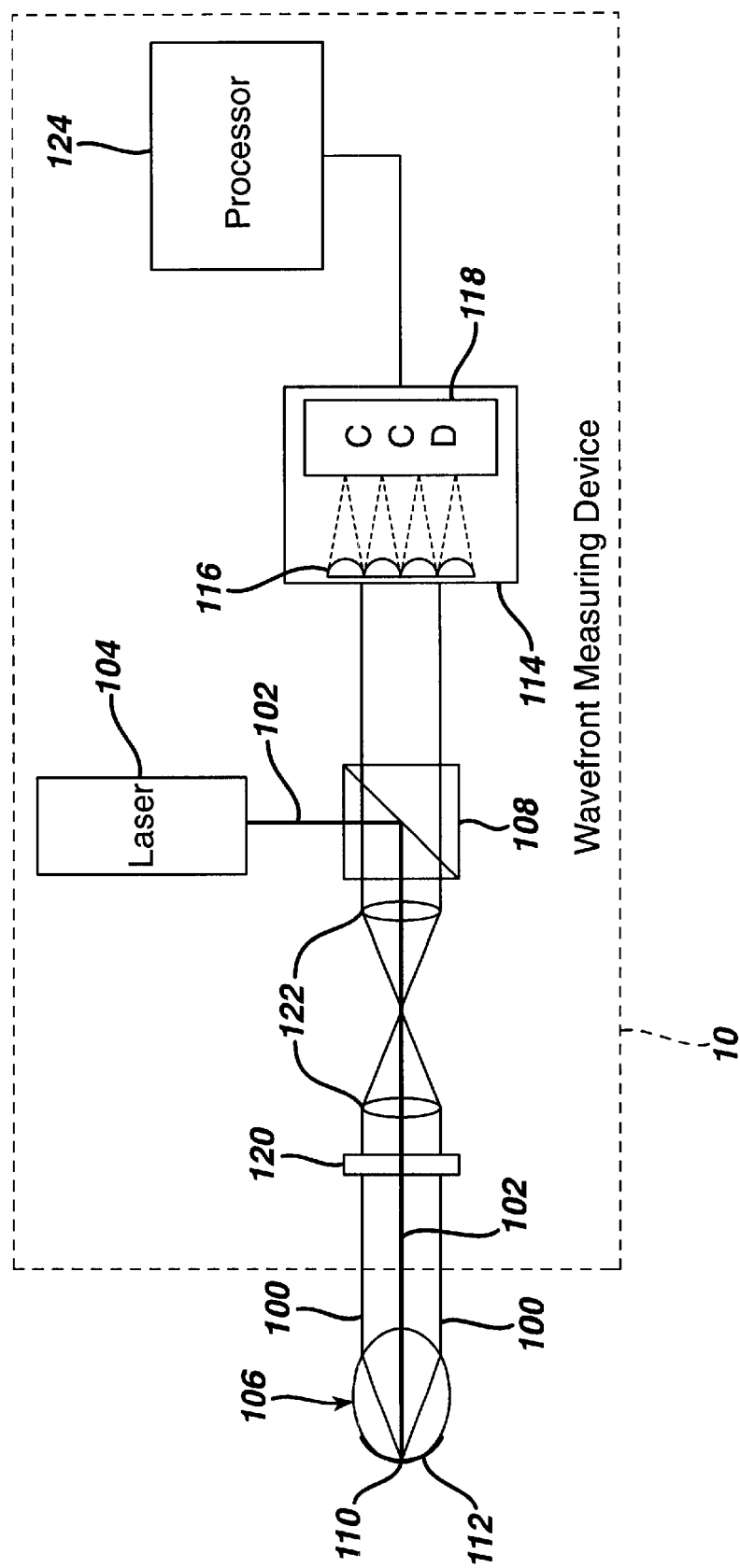
FIG. 1 is a block diagram of a prior art WMD for measuring aberrations introduced by an eye.

An optical combiner 142 places the image projected 133 from the display device 134 into the same path as the input beam 102. The optical combiner 142 can be a dicroic mirror, which passes light of one frequency and reflects light of other frequencies. In one embodiment, the dichroic mirror passes the frequency of light from the radiation source 104 (FIG. 1) and reflects the frequencies of light projected by the projector 138, thereby combining the input beam 102 and the projected image 133 onto the same light path toward the eye 106.

In an alternative embodiment, the image 133 from the display device 134 is not combined with the input beam 102, thereby eliminating the need for the combiner 142. The image 133 is not combined with the input beam 102 if the display device 134 is a monitor or if the WMD 130 is separate from a device including the corrective processor 132, display device 134, and input device 136. Where separate devices are used, the aberrations introduced by the eye 106 are measured by a WMD 130 and stored. Then, a separate device develops a proposed corrective prescription based on the stored aberration measurements, displays the proposed corrective prescription to the patient, and varies the proposed corrective prescription based on feedback from the patient to compute a final preferred corrective prescription for the patient. Various similar alternative embodiments will be readily apparent to those skilled in the art.

Figure 3:
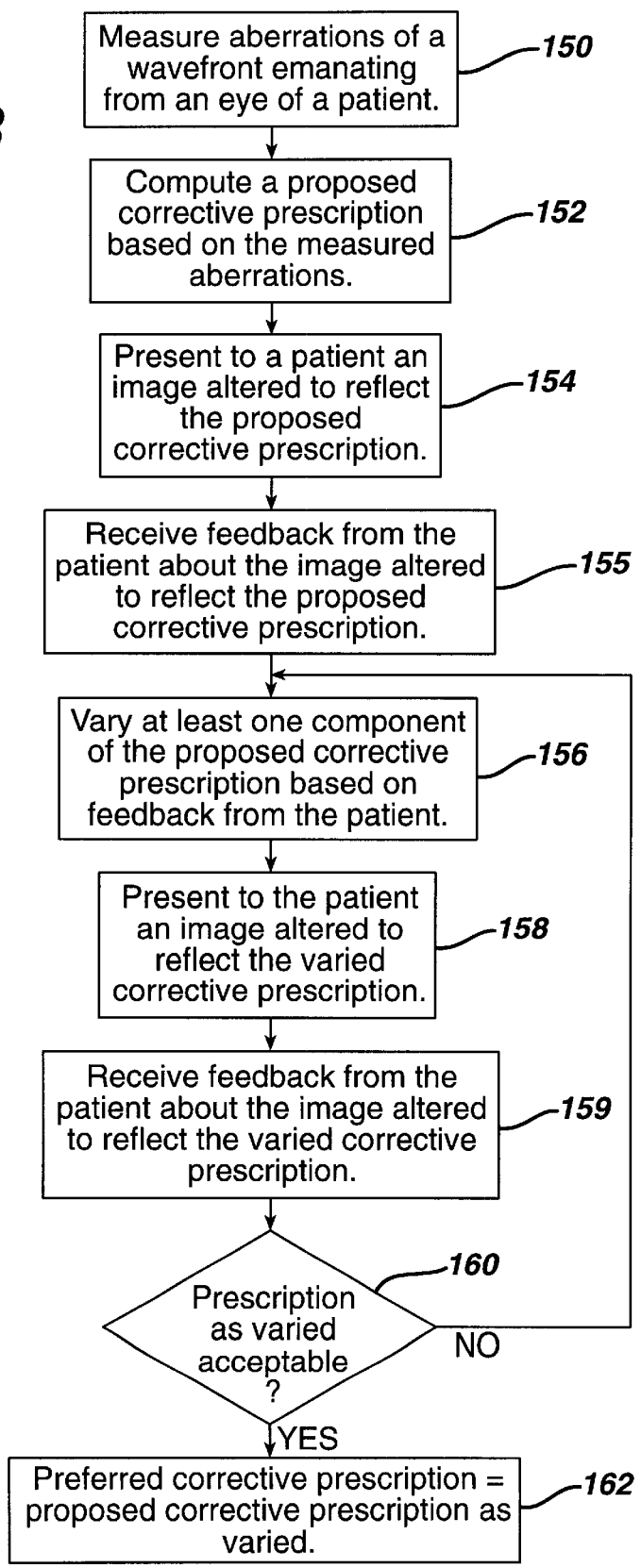
FIG. 3 is a flow chart of a wavefront measuring method for subjectively refining a corrective prescription determined by a WMD in accordance with the present invention.

In use, the wavefront measuring system depicted in FIG. 2 can be used to implement the process depicted in the flow chart of FIG. 3 to subjectively refine a corrective prescription determined by a WMD 130 as now described in detail and with reference to FIG. 2.

At 150, wavefront aberrations of the eye 106 are measured, the WMD 130 being used in the present embodiment.

At 152, a proposed initial corrective prescription is computed based on the wavefront aberrations measured at 150.

The initial proposed corrective prescription is an objective determination of a corrective prescription for the eye 106 prior to subjective feedback from the patient. The proposed corrective prescription can address a plurality of aberration components such as sphere, cylinder, axis, spherical factors, coma factors, trefoil factors, tetrafoil factors, and pentafoil factors as discussed above.

At 154, an image 133 altered to reflect the proposed corrective prescription is presented to the patient via a display device 134. In one embodiment, the image 133 is projected by a projector 138 and then altered by an adaptive optical device 140. The image 133 is then combined with the input beam 102 from the wavefront measuring device 130 by an optical combiner 142 and routed to the eye 106 of the patient.

At 155, feedback about the image altered to reflect the proposed corrective prescription is received from the patient. In one embodiment, the patient provides feedback directly to the corrective processor 132 through the input device 136. For example, if the input device 136 is a joystick, by moving the joystick up/down the patient may affect the cylinder component of a proposed corrective prescription and by moving the joystick left/right the patient may affect the axis component of the proposed corrective prescription. Various alternative embodiments for using input devices 136 to vary components of the proposed corrective prescription will be readily apparent to those skilled in the art. In another embodiment, a third party (e.g., an optometrist) receives feedback from the patient and supplies the feedback to the corrective processor 132 via the input device 136.

At 156, at least one component of the proposed corrective prescription is varied based on the feedback from the patient. Components of the proposed corrective prescription are varied by supplying data to the corrective processor 132 via an input device 136.

At 158, an image 133 altered to reflect the proposed corrective prescription as varied is presented to the patient via a display device 134. In one embodiment, the proposed corrective prescription as varied is presented to the patient in the same manner as described at 154.

At 159, feedback about the image 133 altered to reflect the proposed corrective prescription as varied is received from the patient as described at 155. The feedback may be an indication from the patient that the proposed corrective prescription as varied is acceptable.

At 160, a decision is made regarding whether the proposed corrective prescription as varied is acceptable to the patient. If the proposed corrective prescription as varied is not acceptable or the patient wants to further vary the prescription, processing resumes at 156 and 156–160 are repeated until the proposed corrective prescription as varied is acceptable to the patient. If the prescription is acceptable, processing proceeds at 162.

At 162, the proposed corrective prescription as varied based on feedback from the patient is designated as the preferred corrective prescription for the patient. The preferred corrective prescription is a subjectively refined version of the proposed corrective prescription for the eye 106 based on aberrations determined by the WMD 130. By subjectively modifying the proposed corrected prescription, a corrective prescription that accommodates the psycho-physical aspects associated with vision correction is achieved, thereby resulting in a corrective prescription that is precisely tailored to the patient's visual needs.

FIG. 4 depicts a flow chart of an alternative method for subjectively refining a corrective prescription. The method is similar to the method described in FIG. 4 and similar steps have the same reference number. Accordingly, only the steps which differ from the steps described in FIG. 3 will be described in detail below.

At 164, a conventional refractive eye examination is conducted using a known autorefractor or retinoscope to obtain a first preliminary corrective prescription that includes components for correcting conventional aberrations such as defocus and astigmatism (i.e., sphere, cylinder, and axis). Preferably, the conventional refractive eye examination includes subjectively varying components of the conventional aberrations, such as defocus and astigmatism, to obtain the first preliminary corrective prescription.

At 166, a WMD 130 of a conventional design is used to obtain a second preliminary corrective prescription containing components for correcting nonconventional aberrations such as spherical aberrations, coma, trefoil, tetrafoil, pentafoil, and other irregularities.

At 168, a proposed corrective prescription is computed based on the first preliminary corrective prescription determined at 164 and the second preliminary corrective prescription determined at 166. In one embodiment, computing the proposed corrective prescription includes combining the conventional aberration components of the first corrective prescription with the nonconventional aberration components of the second corrective prescription.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. An apparatus for obtaining a preferred corrective prescription for an eye of a patient, said apparatus comprising:
   a WMD capable of measuring aberrations of the eye;
   a processor in communication with said WMD for determining a proposed corrective prescription which includes one or more components;
   an input device in communication with said processor for varying at least one of said one or more components based on feedback from the patient to obtain the preferred corrective prescription; and
   a display device in communication with said processor for presenting an image to the eye, said image being alterable to reflect said proposed corrective prescription as varied through said input device by varying said at least one of said one or more components.

2. An apparatus in accordance with claim 1, said display device comprising:
   a projector capable of emitting an image;
   an adaptive optical device capable of modifying said image emitted from said projector; and
   wherein said processor is configured to adjust said adaptive optical device based on said proposed prescription as varied based on feedback from the patient.

3. An apparatus in accordance with claim 2, wherein said adaptive optical device comprises a deformable mirror.

4. An apparatus in accordance with claim 1, wherein said display device comprises a monitor.

5. An apparatus in accordance with claim 1, wherein said input device is selected from a group consisting of a keyboard, joystick, microphone, mouse, and light pen.

6. An apparatus for obtaining a preferred corrective prescription for an eye of a patient from aberrations measured by a WMD, said apparatus comprising:

a processor for determining a proposed corrective prescription based on the aberrations measured by the WMD, said proposed corrective prescription including one or more components;

an input device in communication with said processor for varying at least one of said one or more components based on feedback from the patient to obtain the preferred corrective prescription; and a display device in communication with said processor for presenting an image to the eye, said image capable of being altered to reflect said proposed corrective prescription as varied through said input device by varying said at least one of said one or more components.

* * * * *